United States Patent
Lugo Gonzalez et al.

(10) Patent No.: US 9,549,977 B2
(45) Date of Patent: Jan. 24, 2017

(54) USE OF THE PACAP AS A MOLECULAR ADJUVANT FOR VACCINES

(75) Inventors: Juana Maria Lugo Gonzalez, Artemisa (CU); Yamila Carpio Gonzalez, La Habana (CU); Mario Pablo Estrada Garcia, La Habana (CU)

(73) Assignee: CENTRO DE INGENIERIA GENETICA Y BIOTECHNOLOGIA, La Habana (CU)

( * ) Notice: Subject to any disclaimer, the term of this patent is extended or adjusted under 35 U.S.C. 154(b) by 0 days.

(21) Appl. No.: 14/238,377

(22) PCT Filed: Aug. 24, 2012

(86) PCT No.: PCT/CU2012/000004
§ 371 (c)(1),
(2), (4) Date: Apr. 15, 2014

(87) PCT Pub. No.: WO2013/029570
PCT Pub. Date: Mar. 7, 2013

(65) Prior Publication Data
US 2014/0294889 A1 Oct. 2, 2014

(30) Foreign Application Priority Data
Aug. 26, 2011 (CU) ................... 2011/0167

(51) Int. Cl.
*A61K 39/39* (2006.01)
*A61K 39/002* (2006.01)
*A61K 39/12* (2006.01)
*A61K 39/205* (2006.01)
*A61K 39/00* (2006.01)
*A61K 39/02* (2006.01)

(52) U.S. Cl.
CPC ............ *A61K 39/39* (2013.01); *A61K 39/002* (2013.01); *A61K 39/0003* (2013.01); *A61K 39/0208* (2013.01); *A61K 39/12* (2013.01); *A61K 39/205* (2013.01); *A61K 2039/53* (2013.01); *A61K 2039/552* (2013.01); *A61K 2039/55516* (2013.01); *A61K 2039/55566* (2013.01); *A61K 2039/6031* (2013.01); *C12N 2720/10034* (2013.01); *C12N 2760/20034* (2013.01); *C12N 2770/24334* (2013.01)

(58) Field of Classification Search
None
See application file for complete search history.

(56) References Cited

U.S. PATENT DOCUMENTS

| 8,833,306 | B2 * | 9/2014 | Lugo Gonzalez et al. ... | 119/204 |
| 2009/0176703 | A1 * | 7/2009 | Gonzalez ............... | A01K 61/02 514/1.1 |

FOREIGN PATENT DOCUMENTS

WO   WO 9206599 A2 *   4/1992

OTHER PUBLICATIONS

Delgado et al. Vasoactive intestinal peptide and pituitary adenylate cyclase-activating polypeptide inhibit interleukin-12 transcription by regulating nuclear factor kappaB and Ets activation. J Biol Chem. Nov. 5, 1999;274(45):31930-40.*
Baranowska-Bik et al. Can PACAP-38 modulate immune and endocrine responses during lipopolysaccharide (LPS)-induced acute inflammation? Ann N Y Acad Sci. Jul. 2006;1070:156-60.*
Weintraub A. Immunology of bacterial polysaccharide antigens. Carbohydr Res. Nov. 14, 2003;338(23):2539-47.*
"Anti-LPS Antibody Products" (internet publication, http://www.biocompare.com/pfu/110447/soids/1801/Antibodies/LPS).*

* cited by examiner

*Primary Examiner* — Nick Zou
(74) *Attorney, Agent, or Firm* — Hoffmann & Baron, LLP

(57) ABSTRACT

The present invention relates to the use of the pituitary adenylate cyclase activating peptide (PACAP) as a molecular adjuvant for vaccines. Among other applications, these vaccines may be used in the protection against infectious agents such as viruses, bacteria and ectoparasites affecting mammals, birds and aquatic organisms. The PACAP, combined with a particular antigen, demonstrates its effectiveness as adjuvant increasing the host immune response against that antigen. This type of response can be observed when the vaccine compositions or combinations that include PACAP are administered orally, by injection, or by immersion baths, in case of aquatic organisms.

12 Claims, 3 Drawing Sheets

USE OF THE PACAP AS A MOLECULAR ADJUVANT FOR VACCINES

This application claims priority based on an International Application filed under the Patent Cooperation Treaty, PCT/CU2012/000004, filed Aug. 24, 2012, which claims priority from Cuban Application No. 2011-0167, filed Aug. 26, 2011, each of which are incorporated herein by reference.

TECHNICAL FIELD

The present invention relates to the field of medicine, molecular biology and immunology, specifically, with the development of vaccines and adjuvant for vaccines. In particular, the present invention discloses the use of the pituitary adenylate cyclase activating peptide (PACAP) as a molecular adjuvant for vaccines, which are used in immunization strategies.

BACKGROUND OF THE INVENTION

The main objective of vaccination is to induce a specific and effective immune response against a pathogen that also produces protection against infection and/or a disease and results in its elimination. The concept that the immune response against a particular antigen can be improved by the addition of certain compounds in the vaccine formulation was shown about 100 years ago, when the aluminum salts were introduced into the formulations and were called "adjuvant" (G. Leroux-Roels (2010) Vaccine 28S C25-C36).

Traditional vaccines consist of inactivated or attenuated pathogens, or toxins derived from these microorganisms. Although the use of inactivated or attenuated pathogens has high immunogenicity, currently is unattractive in vaccinology because of the high toxicity of these preparations.

Therefore, there is growing interest in adjuvants in the research related to the development of new generations of vaccines based on recombinant protein subunits, synthetic peptides and deoxyribonucleic acid (DNA) plasmids. These new vaccine variants, although less toxic, are mostly less immunogenic when they are administered without an immunostimulatory adjuvant. Due to this reason, in recent years has increased the need for safer and more potent adjuvants (Saenz et al. (2010) Vaccine 28 (47): 7556-7562).

Although the use of adjuvant is well known, the manner in which they act is less clear. It is considered that, in general, they increase the effectiveness of vaccines through several mechanisms including: 1) increased antigen processing and presentation by dendritic cells, 2) induction of a "danger" signal by signaling pathways mediated by receptors that recognize patterns associated pathogens, such as the "Toll" receptors, and 3) by activating co-stimulatory signals that activate lymphocytes. These mechanisms are triggered by cytokine induction and up-regulation of the expression of appropriate co-stimulatory signals (Secombes (2010) Fish & Shellfish Immunology, 409-416).

Several endogenous molecules and proteins (Yin and Kwang (2000) Fish & Shellfish Immunology 10, 375-378; Lingnau et al. (2007) Expert Rev Vaccines 6 (5): 741-6; Zhang et al. (2010) Vaccine 28: 5114-5127) have been studied as adjuvants. Also, it is known that certain immunostimulating peptides can act as an adjuvant in vivo, stimulating the immune response of protein or peptide antigens (Saenz et al. (2010) Vaccine 28 (47): 7556-7562).

PACAP belongs to the superfamily of secretin/glucagon/vasoactive intestinal peptide (Miyata et al (1989) Biochem Biophys Res Commun 164: 567-574). It is a multifunctional neuropeptide which plays important roles as neurotrophic and hypophysiotropic factor, as a neurotransmitter, neuromodulator and vasodilator molecule in mammals (Arimura A. (1998) Japanese Journal of Physiology 48: 301-31). It has been demonstrated its role in the cell division and differentiation and also in the cell death (Sherwood et al. (2000) Endocrine Review 21: 619-670). This peptide exists in two molecular forms of 38 (PACAP38) and 27 (PACAP27) amino acids (Miyata et al. (1990) Biochemical and Biophysical Research Communications 170:643-8). The biological actions of PACAP are exerted through a family of three VIP/PACAP receptors that belong to the secretin G-protein-coupled receptor: the type I receptor, which is highly specific for PACAP and is named as PAC-1; and type II receptors, which exhibit the same affinity for PACAP than for vasoactive intestinal peptide (VIP), which are known as VPAC-1 and VPAC-2 (Vaudry et al. (2000) Pharmacol Rev 52: 269-324).

PACAP is widely distributed in various tissues, including those related to the immune system, although the presence of this peptide and its receptors in cells of the immune system in mammals has only been partially elucidated (Gaytan et al. (1994) Cell Tissue Res 276:223-7, Abad et al. (2002) Neuroimmunomodulation 10:177-86). PACAP modulates the inflammatory response through the regulation of the interleukin-6 (IL-6) and interleukin-10 (IL-10) (Martinez et al. (1996) J Immunol 156 (11):4128-36; Martinez et al. (1998) J Neuroimmunol 85 (2): 155-67), Martinez et al. (1998) J Leukoc Biol 63 (5): 591-601).

In activated macrophages, PACAP inhibits the production of pro-inflammatory cytokines and stimulates the production of anti-inflammatory cytokines, thus allowing the homeostasis of the immune system. Additionally, it is known that PACAP reduces the expression of the co-stimulatory molecules B7.2/B7.1 and the subsequent activation of T helper cells (Th). On the other hand, PACAP inhibit in activated macrophages the production of IL-6 through its PAC-1 receptor, suppressing inflammation (Martinez et al. (1998) J Neuroimmunol 85 (2): 155-67, Martinez et al. (1998) J Leukoc Biol 1998, 63 (5): 591-601). The inhibitory action of PACAP over IL-6 transcription in response to intense inflammatory stimuli helps the tissue protection and the immune system homeostasis (Martinez et al. (1998) J Neuroimmunol 85(2):155-67; Martinez et al. (1998) J Leukoc Biol. 1998 May; 63(5):591-601). In contrast, PACAP induce the expression of B7.2 and promotes cellular differentiation to Th2 in non-stimulated macrophages (Delgado and Ganea (2001) Arch Immunol Ther Exp (Warsz) 49(2):101-10). The presence of PACAP in the lymphoid organs of ducks has been reported (Squillacioti et al. (2005) Anatomia, Histologia, Embryologia. Volume 34, Issue Supplements 1, page 49).

The use of PACAP in mammals, as a therapeutic agent for treating autoimmune diseases such as septic shock, rheumatoid arthritis and Crohn's disease, has been proposed (Gomariz et al. (2006) Ann. NY Acad. Sci 1070: 51-74). It is known that in autoimmune diseases there is an uncontrolled immune response against substances and tissues of the organism. In this regard, PACAP prevents inflammation in animal models of autoimmune diseases, through a proper balance of cytokines and chemokines and its receptors, through the recruitment of immune cells and by regulating the generation and activation of Th1 cells and the cytokines which these cells secrete.

Moreover, it is known that molecules involved in the immune system homeostasis, such as "Toll" receptors, are essential for activation of the innate immune response, which boosts the adaptive immune response. However, this response may lead to the pathogenesis of acute and/or chronic inflammation, autoimmunity, and cancer (Gomariz et al. (2010) Current Pharmaceutical Design 16: 1063-1080). In this regard, it is known that the VIP-PACAP system is involved in the regulation of the expression of genes encoding these receptors (Gomariz et al. (2006) Ann. NY Acad. Sci 1070: 51-74). Therefore, both peptides may induce disturbances in the regulation pathways of production of these receptors.

PACAP attenuates the circulating levels of cytokines mediated by the endogenous molecule HMGB1 (high mobility group box 1) (Tang et al. (2008) International Immunopharmacology 8 (12): 1646-1651), and inhibits their release. It is known that HMGB1 molecule and its derived peptides are capable of acting as adjuvant, enhancing the immune response against a peptide antigen and protein (Saenz et al. (2010) Vaccine 28 (47): 7556-7562).

The knowledge about the function of PACAP in the modulation of the fish immune response is limited to studies performed by our research group. We demonstrated that the recombinant *Clarias gariepinus* PACAP administered by immersion baths or by injection not only promotes growth but also stimulates innate immune parameters (lysozyme, nitric oxide derived metabolites and antioxidant defenses) and acquired immunity (IgM) in larvae and juveniles fish (Carpio et al. (2008) Fish and Shellfish Immunology 25:439-45; Lugo et al. (2010) Fish and Shellfish Immunology 29:513-520). These properties of PACAP were described in the international patent application WO2007/059714, "Neuropéptidos para el cultivo de organismos acuáticos".

At present, in the field of human and veterinary medicine, there is still interest in identifying compounds that may be used as safe and more potent adjuvants that may be incorporated into existing vaccines, and in those which are under development.

DETAILED DESCRIPTION OF THE INVENTION

The present invention solves the above described problem, providing a new alternative of adjuvant capable of strongly potentiate the immune response towards an antigen that is co-administered, and hence it constitutes a highly effective adjuvant. It is an object of the present invention, the use of "pituitary adenylate cyclase activating peptide" (PACAP) as a molecular adjuvant for antigens that are present in vaccines used in different immunization strategies. In one embodiment of the invention said vaccines, comprising PACAP as an adjuvant, are designed for immunization against infectious agents. These infectious agents can be viruses, bacteria and ectoparasites, among others. In a particular embodiment, these infectious agents affect mammals, birds and fish.

The term "pituitary adenylate cyclase activating polypeptide (PACAP)", as used in the present invention, includes this molecule in any variant (PACAP27 or PACAP38), either isolated from its natural source, produced by chemical synthesis, or produced by recombinant DNA technology; and it includes its use as a peptide or in the form of nucleic acids.

In the context of this invention the term "molecular adjuvant" refers to any molecule of protein nature capable of modulating the immune response against a vaccine antigen, increasing it.

Up to now none research has demonstrated the use of PACAP as a molecular adjuvant. As stated above, it has been proposed to use this peptide in mammals as a therapeutic agent for treating autoimmune diseases, such as septic shock, rheumatoid arthritis and Crohn's disease (Gomariz et al. (2006) Ann. NY Acad. Sci. 1070: 51-74). In this regard, PACAP prevents inflammation in animal models of autoimmune diseases through a proper balance of cytokines and chemokines and their receptors, through the recruitment of immune cells and by regulating the generation and activation of the Th1 cells and the cytokines that these cells secrete. Given these findings, is unexpected the effect of PACAP found as part of our studies, showing that its administration in combination with an antigen increases the immune response against said antigen, through the stimulation of the pro-stimulatory cytokines and other elements of the humoral immune response.

Moreover, it is known that the VIP-PACAP system is involved in the regulation of the expression of genes encoding the "Toll" receptors (Gomariz et al. (2006) Ann. NY Acad. Sci 1070: 51-74). In this sense, both peptides may induce disturbances in the regulation pathways of production of these receptors, which makes non obvious its use as a vaccine adjuvant. Another element contrasting with the new use of PACAP, disclosed in this invention, is the demonstration that this peptide attenuates the circulating levels, and inhibits the release, of cytokines mediated by the endogenous HMGB1 molecule (Tang et al. (2008) International Immunopharmacology 8 (12): 1646-1651).

In the present invention it is demonstrated, for the first time, that the increase in the immune response specific to the vaccine antigen co-administered with PACAP is observed both at the level of the humoral and the cellular immune response. Another object of the present invention is a vaccine composition comprising PACAP as an adjuvant, at least a vaccine antigen, and pharmaceutically acceptable vehicles or diluents. This vaccine composition containing PACAP as an adjuvant and at least one antigen of interest causes an immune response against the antigen or the antigens that is either local or systemic. The vaccines or vaccine compositions of the present invention may be based, for example, in recombinant proteins, attenuated microorganisms or nucleic acids. In one embodiment of the invention the mentioned vaccine compositions are administered orally, by injection or by immersion baths.

In the context of the present invention, in such vaccine compositions, PACAP is administered as a peptide isolated from its natural source, obtained by chemical synthesis or by recombinant DNA technology. PACAP can also be employed as nucleic acids.

In different embodiments of the present invention the vaccines comprising PACAP in combination with several antigens are administered to mammals, birds and fish, showing, for the first time, an adjuvant effect for PACAP. Unexpectedly, it was observed that the administration of the neuropeptide PACAP combined with an antigen increased the levels of specific antibodies against said antigen in mammals, birds and fish. Additionally, it was demonstrated in vitro, for the first time, that PACAP significantly increases the transcripts of interleukin 1 beta (IL 1□) and interleukin 15 (IL15) in fish leukocytes.

In different embodiments of the present invention, that disclose vaccine compositions or combinations comprising PACAP as an adjuvant, diverse antigens are used, such as ovalbumin (OVA), the E2 glycoprotein of the Classical Swine Fever Virus (CSFV), hemagglutinin (HA) of the avian influenza virus, the polypeptide my32 of *Caligus rogercresseyi*, inactivated cells of *Aeromonas hydrophila*, the 106 kDa polyprotein (NH2-VP2-VP4VP3-COOH) of the Infectious Pancreatic Necrosis Virus (IPNV), the G glycoprotein of the Viral Hemorrhagic Septicemia Virus (VHSV) and the ciliate parasitic *Ichthyophthirius multifiliis*.

In a particular embodiment of the invention, in the vaccine compositions, PACAP is applied as a formulated feed, at a concentration of 50-750 µg/kg of feed. In a second embodiment of the invention, PACAP is applied by injection, at a concentration of 0.1-10 µg per gram of body weight. In another embodiment of the invention, PACAP is applied in aquatic organisms by immersion baths, at a concentration of 50-1000 µg per liter of water.

In another embodiment of the invention, the antigen and the adjuvant PACAP may be part of a vaccine combination whose elements are administered simultaneously, separately or sequentially during the same immunization protocol. In a particular embodiment of the invention, the combination is used in the prevention of viral, bacterial and parasitic diseases. For this vaccine combination, PACAP and the antigen, or antigens, are administered orally, by injection or by immersion baths.

In a particular embodiment, the PACAP is applied as formulated feed, at a concentration of 50-750 µg/Kg of feed. In a second embodiment, the PACAP is applied by injection, at a concentration of 0.1-10 µg of peptide per gram of body weight. In another embodiment of the invention, PACAP is applied to fish by immersion baths, at a concentration of 50-1000 µg of PACAP per liter of water.

Another aspect of this invention is a method for increasing the immune response against an antigen wherein is employed a vaccine composition comprising the "pituitary adenylate cyclase activating peptide" (PACAP) as an adjuvant for said antigen. According to the method disclosed in the invention, the PACAP as an adjuvant and the antigen can be administered simultaneously, separately or sequentially during the same immunization schedule. PACAP is used as adjuvant in the method of the invention as a peptide which has been obtained from its natural source, by chemical synthesis or by the recombinant DNA technology. Also the invention comprises a method wherein the PACAP used as an adjuvant is administered in the form of nucleic acids. According to the method of the invention, the increase in the immune response specific to the vaccine antigen co-administered with PACAP takes place both in the humoral and the cellular specific immune response.

As demonstrated in several embodiments of the invention, the enhancement or increase in the immune response against the antigen of interest is expressed as higher levels of protection against various infectious agents; including viral, bacterial and ectoparasite entities.

EXAMPLES

Example 1

Effect of the Co-Immunization with OVA and PACAP on the Humoral Immune Response in Mice BALB/c mice (n=12) with a body weight of 20 g were separated into two experimental groups of 6 animals each one. The negative control group (PBS/OVA) was intraperitoneally injected, on days 0 and 7 with a dose of 6 µg of OVA in 0.2 mL of PBS. The group treated with PACAP38 (PBS/OVA+peptide) was intraperitoneally injected on days 0 and 7 with a dose of 6 µg of OVA+0.5 µg of PACAP38 in 0.2 mL of PBS. On day 15 of the immunization protocol, blood from each fish was taken in order to evaluate total IgG, IgG1 and IgG2a titers.

Figure 1:
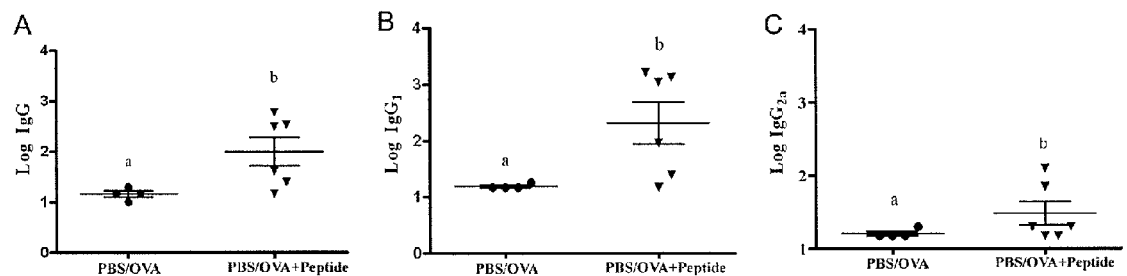
FIG. 1. Titles of total immunoglobulin G (IgG) (A), IgG1 (B) and IgG2a (C) induced in mice by immunization with OVA co-administered with the neuropeptide PACAP38. Two experimental groups of 6 animals each one were used. The negative control group (phosphate buffered saline (PBS)/OVA) was inoculated intraperitoneally on day 0 and 7 with a dose of 6 µg of OVA in 0.2 mL of PBS. The group that also received PACAP38 (PBS/OVA+peptide) was inoculated intraperitoneally on day 0 and 7 with a dose of 6 µg of OVA+0.5 µg of PACAP38 in 0.2 mL of PBS. Different letters indicate significant differences.

The FIGS. 1A, B and C show the total IgG, IgG1 and IgG2a titers, respectively, induced by immunization of mice with OVA co-administered with PACAP38. Animals in the group PBS/OVA+peptide showed a specific total IgG titer against OVA statistically superior compared with the control group (FIG. 1A). Similarly, we observed that the titles of IgG1 and IgG2a specific against OVA in the group immunized with OVA+PACAP were significantly higher than those observed in the group immunized with OVA only (FIGS. 1B and C).

Example 2

Figure 2:
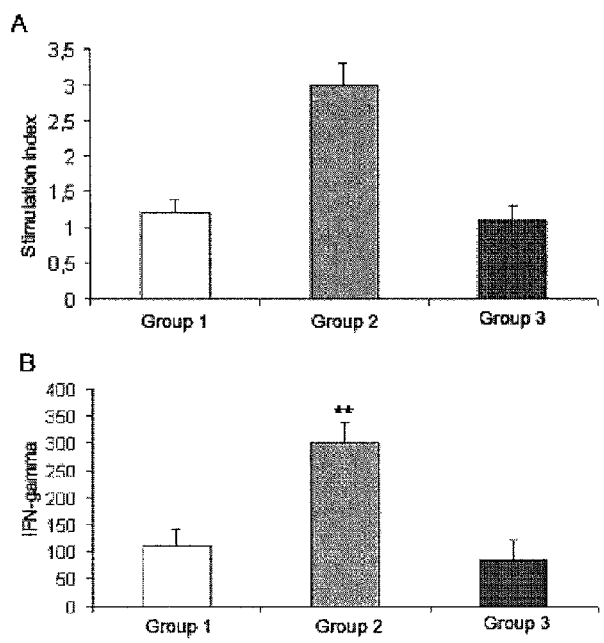
FIG. 2. Assessment of the cellular immune response in pigs vaccinated with the vaccine composition based on E2-PACAP. The cellular immune response was measured in pig lymphocytes isolated on day 5 after vaccination with E2 (group 1), with E2+PACAP (group 2) and with placebo (group 3). (A) lymphoproliferation assay: the results are expressed as stimulation index (SI), defined as the ratio between counts per minute (cpm) of the stimulated culture (cpm) and cpm of the untreated control group. The lymphoproliferative response with an SI≥2 was considered positive (B) IFN-γ secretion determination by real time PCR. Values are expressed as the arithmetic mean of $2^{-\Delta\Delta Ct}$. (**) $p<0.01$.
Figure 3:
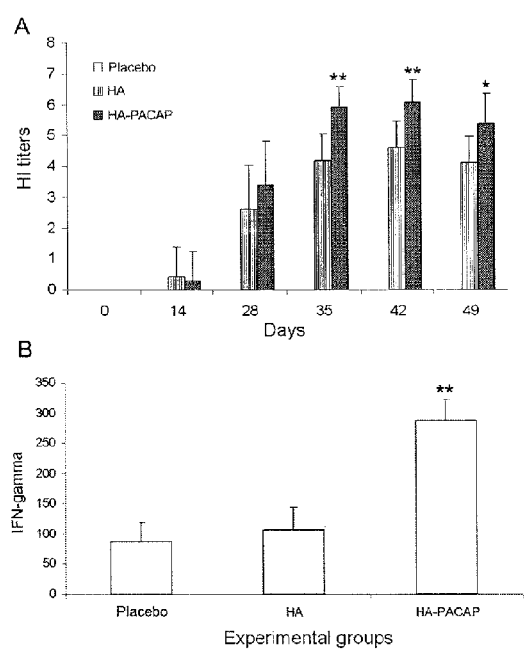
FIG. 3. Titers of hemagglutination inhibition in chickens immunized with HA or HA-PACAP (A). The arithmetic mean of the antibody titers were expressed as the $\log_2$ of the reciprocal value of the highest dilution of serum which produced hemagglutination inhibition. (B) Cellular immune response in immunized chickens. The IFN-γ secretion was determined by real-time PCR. Values are expressed as the arithmetic mean of $2^{-\Delta\Delta Ct}$. (**) $p<0.01$.

Evaluation of Cellular Immune Response in Pigs Vaccinated with the Vaccine Composition Based on E2-PACAP The antigen E2 is the major envelope glycoprotein of the CSFV. In order to evaluate the cellular immune response in pigs vaccinated with the vaccine composition based on E2-PACAP, and to compare its response with that produced by the E2 antigen we selected 18 healthy pigs of 20 kg average weight and serologically negative to CSFV, from a farm with no history of this disease and non-vaccinated against CSFV in the 3 preceding years. The pigs were located into 3 different groups of 6 animals each one, with water and food ad libitum. Each vaccine composition was applied in single immunization as follow: 25 µg of recombinant E2 (Group 1) and 25 µg of E2 co-administered with a similar amount of PACAP38 (Group 2). Group 3 was established as a placebo group. The immunogens were formulated in an emulsion of oil adjuvant and inoculated by intramuscular injection at a final volume of 2 mL. The animals were challenged on day 8 post-immunization by intramuscular injection of the CSFV ($10^5$ LD$_{50}$ of the "Margarita" isolation). We conducted a daily analysis of clinical signs and blood samples were taken on days 3 and 5 to assess lymphocyte proliferation and the expression of the IFN-γ as indicators of cellular immune response. In the animals immunized with E2-PACAP was detected an increase in the lymphocyte response (FIG. 2A) and the highest levels of IFN-γ on day 5, as compared with the other groups (FIG. 2B). This results show that the co-administration of the E2 antigen with PACAP produces a cellular immune response against CSFV in pigs.

Example 3

Effect of the Co-Immunization of the HA of the Avian Influenza Virus (Virus A/VietNam1203/2004) and PACAP on the Humoral and Cellular Immune Response in Chickens For immunization were used white leghom chickens of 3 weeks of age. Three experimental groups of ten chicks each were employed.

Group 1: injected with 20 μg of HA

Group 2: injected with 20 μg of HA+0.5 μg of PACAP27

Group 3: injected with 20 μg of bovine serum albumin

The HA was obtained by recombinant expression in mammalian cells. The vaccines were formulated with Montanide 888 and were administered in a final volume of 0.5 mL by subcutaneous route. The animals were re-immunized at day 28 post-immunization. Blood samples were taken at days 0, 14, 28, 35, 42 and 49, in order to evaluate the titers of protective antibodies using a haemagglutination inhibition assay and also to isolate leukocytes to evaluate the cellular immune response produced by the vaccines in vitro.

The chickens immunized with HA-PACAP showed a superior antibody response compared with the group immunized with HA, from day 35 of the re-immunization (FIG. 3A). The group treated with HA-PACAP showed an increase in the cellular immune response, measured as stimulation of IFN-γ, in comparison to the groups immunized with HA or the control group (FIG. 3B).

Example 4

Effect of PACAP on the Expression of IL1-β and IL15 in Peripheral Blood and Anterior Kidney Leukocytes of Neïve Rainbow Trout (*Oncorhynchus mykiss*)

We used juvenile rainbow trout (*O. mykiss*) of approximately 50 g, free of the VHSV and IPNV. Fish (n=5) were anesthetized with methanesulfonic acid salt (Sigma, USA) and peripheral blood from the tail vein was taken aseptically of each fish and then the head kidney was collected.

Peripheral blood and the head kidney leukocytes were isolated following the method described by Graham and Secombes (Graham and Secombes (1998) Immunology 65:293-7).

The cells were resuspended in L-15 with 5% FCS at a concentration of $5\times10^6$ cells per ml and dispensed in 24-well plates at 1 mL per well. The leukocytes were treated with 3 doses of *Clarias gariepinus* PACAP38 ($10^{-10}$ M, $10^{-9}$ M and $10^{-8}$ M) obtained by chemical synthesis, in duplicate. Untreated leukocytes dispensed in duplicate were used as negative control.

The levels of IL 1β and IL 15 were evaluated 48 hours after treatment. In order to achieve this objective, total RNAs were purified from leukocyte cultures treated with PACAP by the method described by Chomczynski and Sacchi (Chomczynski and Sacchi (1987) Anal. Biochem. 162:156-9).

Because of the designed primers to amplify IL 1β and IL 15 do not discriminate between cDNA and genomic DNA, total RNAs purified from different tissues were treated with a DNA nuclease, specifically with the RQ1 RNase-free DNase (Promega).

For cDNA synthesis was used a commercial kit that use the SuperScript III reverse transcriptase (Invitrogen). Finally, for quantitative PCRs (qPCRs) was used a commercial mixture of PCR: Power SYBR Green PCR Master Mix (Applied Biosystems). The results of qPCR were normalized against an endogenous gene of constitutive expression, specifically against the elongation 1α factor (EF 1α) and were performed in triplicate. The results were expressed as $2^{-\Delta Ct}$, where ΔCt is equal to the remainder of the Ct value of the target gene minus the Ct value of the normalized gene EF 1α.

Figure 4:
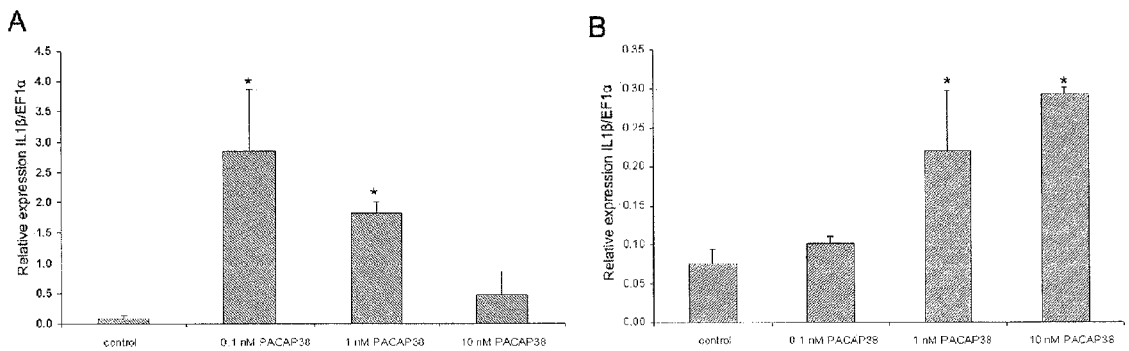
FIG. 4. Expression analysis by real time PCR of the in vitro effect of PACAP38 over the transcription of IL 1β in peripheral blood leukocytes (A) and head kidney (B) of naïve rainbow trout. The effects of PACAP administration at a concentration of $10^{-10}$ M, $10^{-9}$ M and $10^{-8}$ M was evaluated at 48 h post-treatment. The experiment was repeated 4 times. The leukocyte cultures were treated in duplicates and the PCRs were performed in triplicate. Data are expressed as mean of relative expression of IL 1β related to the endogenous elongation factor EF1α±standard deviation (SD). (*) $p<0.05$). * ($p<0.05$) indicates that the relative expression of the gene of interest was statistically higher compared to its relative expression in untreated leukocyte cultures (negative control).

The IL 1β protein levels increased after 48 hours of treatment in peripheral blood leukocytes treated with $10^{-10}$ M of PACAP38. At a dose of $10^{-9}$ M, there is also a stimulatory effect of PACAP38 on the transcription of IL 1β compared with the negative control group, but the expression levels detected in this case were below to those obtained with the dose of $10^{-10}$ M. These results show a positive effect of PACAP38 on the transcription of IL 1β at low concentrations ($10^{-9}$ M and $10^{-10}$ M) (FIG. 4A). In head kidney leukocytes, the effect of PACAP 38 on the IL1β transcription was moderate compared to those obtain in peripheral blood leukocytes, showing a stimulatory effect only at a dose of $10^{-9}$ M (FIG. 4B).

Figure 5:
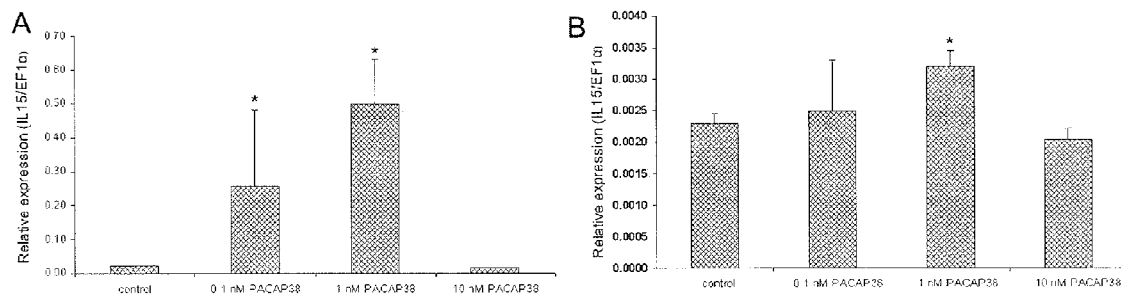
FIG. 5. Expression analysis by real time PCR of the in vitro effect of PACAP38 over the transcription of IL 15 in peripheral blood leukocytes (A) and head kidney (B) of naïve rainbow trout. The effects of PACAP administration at a concentration of $10^{-10}$ M, $10^{-9}$ M and $10^{-8}$ M was evaluated at 48 h post-treatment. The experiment was repeated 4 times. The leukocyte cultures were treated in duplicates and the PCRs were performed in triplicates. Data are expressed as the mean of the relative expression of IL 15 related to the endogenous elongation factor EF1α±standard deviation (SD). (*) $p<0.05$.

Additionally, we observed a stimulatory effect of PACAP38 on the expression of the IL 15 in peripheral blood leukocytes stimulated with PACAP at a doses of ($10^{-10}$ M and $10^{-9}$ M). The highest values were obtained at a dose of $10^{-10}$ M (FIG. 5A). In head kidney leukocytes, as it was previously observed with the IL1β transcription the effect was moderate. The IL 15 expression levels in the PACAP treated group were statistically higher than the negative control group at the dose of $10^{-9}$ M (FIG. 5B).

Example 5

Controlled Challenge Test with *Caligus Rogercresseyi* in *Salmo Salar* Previously Immunized Intraperitoneally with the Antigen My32, and My32 Co-Administered with PACAP My32 protein was obtained in recombinant form, in the pellet of broken BL21(DE3)-pET28a-my32 transformed *E. coli* cells. It is known that this protein, administered intraperitoneally (IP), produced a 57% inhibition of infection in the second generation of parasites in a challenge test with *C. rogercresseyi* in *S. salar* (Carpio et al. (2011) Vaccine. 29 (15):2810-20).

To demonstrate the adjuvant effect of PACAP on this protein, we designed a vaccination-challenge experiment in *S. salar* under controlled conditions. In this experiment were established six experimental groups of 25 animals (average weight 80 g) each one:
Group 1: Injected IP with PBS
Group 2: Injected IP with PACAP38 at the dose of 1 µg/fish
Group 3: Injected IP with my32 at the dose of 3 µg/g of body weight (gbw)
Group 4: Co-administration by IP injection of my32 at 3 µg/gbw and PACAP at the dose of 1 µg/fish
Group 5: Fish injected IP with my32 at the dose of 3 µg/gbw and fed with 250 µg of PACAP/Kg of feed daily, for one week before and after de immunization with my32.

During the course of the experiment, fish were fed twice daily with a commercial formula without PACAP at the rate of 1% of their body weight, with the exception of the group 5, which was provided one week before and after immunization the same commercial formula with PACAP, as described by Adelmann et al. ((2008) Vaccine 26, 837-844) for oral administration of an attenuated strain of the virus VHSV.

After 500 arbitrary thermal units, fish were adapted to seawater for two weeks. Subsequently, they were challenged with 2000±200 copepodites to each tank. The fish were kept without water flow in the dark and under conditions of temperature, salinity, and oxygen suggested by Stone et al. (Dis Aquat Organ, 2000, 41: 141-149) for 24 days. Turnover and filtration was performed manually every 48 hours. At 24 days, fish were anesthetized and killed for parasite counting under a stereomicroscope. The results in Table 1 show a reduction in infestation levels in the groups treated with PACAP, my32 and PACAP+my32. The largest reduction occurred in groups 4 and 5, which shows the adjuvant effect of PACAP on the antigen.

TABLE 1

Count of parasites 24 days post-challenge with *C. rogrecresseyi*

| Experimental groups | Number of parasites/fish | Inhibition of the infestation (%) |
|---|---|---|
| PBS | 37 ± 3$^a$ | — |
| PACAP | 29 ± 5$^b$ | 22 |
| my32 | 17 ± 8$^c$ | 55 |
| PACAP-IP + my32-IP | 8 ± 3$^d$ | 79 |
| PACAP-oral + my32-IP | 5 ± 2$^e$ | 86 |

Letters indicate statistical significant differences
Percent of inhibition of infestation calculated as (1 − T/C) × 100 (T: parasite number per fish in vaccinated group, C: parasite number per fish in placebo group).

Example 6

PACAP Adjuvant Effect on the Humoral Immune Response in Common Carp (*Cyprinus Carpio*) Versus *Aeromonas Hydrophila*

The experiment was performed with carp (*C. carpio*) 40±10 g. These aquariums were maintained in 600 L at a temperature of 28±2° C. Three experimental groups of 10 carps each one were established and they were injected intraperitoneally with the following immunogens:
Group 1: PBS
Group 2: Inactivated cells of *A. hydrophila*
Group 3: Inactivated cells of *A. hydrophila* plus 1 µg per fish of PACAP38.

Figure 6:
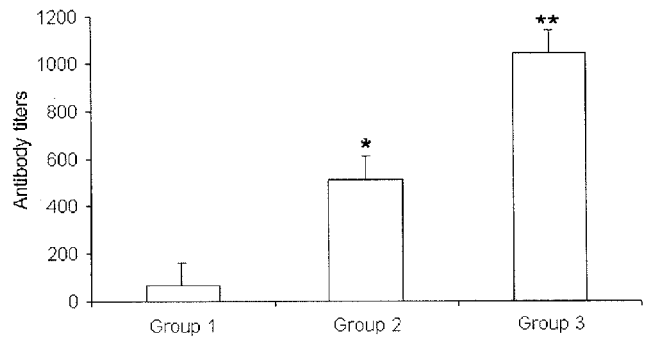
FIG. 6. Agglutinating antibody titers against *A. hydrophila* in common carp. Values in the Y axis represent the arithmetic mean of the antibody titers±standard error. (*) $p<0.05$, (**) $p<0.01$. Group 1: injected with PBS, Group 2: injected with formalin inactivated *A. hydrophila* cells, Group 3: injected with formalin inactivated *A. hydrophila* cells and PACAP (1 µg/fish).

The fish were injected on day 0 and 14, and blood was collected from the caudal vein on days 0 and 21. The results showed that agglutinating antibody titers were significantly higher in the group immunized with the bacterium plus PACAP compared with the group immunized with the bacteria alone (FIG. 6). These results demonstrate the effect of PACAP as a molecular adjuvant. The cell preparation of *A. hydrophila* and the antibody titers measurements were made according to Yin et al. ((1996) Fish & Shellfish Immunology 6, 57-69).

Example 7

Controlled Challenge Test with *A. Hydrophila* in Common Carp (*C. Carpio*) Previously Immunized Intraperitoneally with Inactivated Bacteria and Inactivated Bacteria Co-Administered with PACAP The experiment was performed with common carp (*C. carpio*) 30±5 g. The fish were maintained in 250 L aquariums at a temperature of 30±2° C. Three experimental groups were established with 20 carps each one, which were injected intraperitoneally.

Group 1: PBS
Group 2: Inactivated cells of *A. hydrophila*
Group 3: Inactivated cells of *A. hydrophila* plus 1 µg of PACAP38 per fish.

The fish were injected on day 0 and 14. On day 21 the challenge was performed by injecting IP $LD_{50}$ of the bacterium and the mortality was recorded during 7 days. We calculated the relative percent survival (RPS) as:

RPS(%)=(% mortality controls–% mortality-treated)/(% mortality controls)×100

The result was 65% in the Group 2 and 95% in the Group 3, which demonstrates that administration of PACAP increases the survival rate of vaccinated and challenged fish to the pathogen.

Example 8

Effect of the Co-Administration of PACAP with a DNA Vaccine Based on the Gene Encoding the 106 kDa Polyprotein (VP2-VP4VP3-NH2-COOH) of IPNV, in the Rainbow Trout (*Oncorhynchus Mykiss*) Experimentally Challenged with this Virus An experiment was conducted to evaluate the effect of the intramuscularly co-administration of PACAP with a DNA vaccine based on the gene encoding the 106 kDa polyprotein (VP2-VP4VP3-NH2-COOH) of the IPNV in rainbow trout challenged experimentally with this virus. Six experimental groups were conformed of 15 fish each one (12±1 g) and were kept in water at 10-12° C.:

Group 1: Fish injected with PBS.
Group 2: Fish injected with the DNA vaccine (pP-IPNV) at a dose of 1 µg/fish.
Group 3: Fish co-injected with the DNA vaccine (pP-IPNV) at a dose of 1 µg/fish and a plasmid having the cDNA sequence of *C. gariepinus* PACAP under the control of the immediate early promoter of the human cytomegalovirus (pCMV-PACAP) at a dose of 0.5 µg of pCMV-PACAP/fish.
Group 4: Fish co-injected with pP-IPNV vaccine (1 µg/fish) with a negative control plasmid at a dose of 0.5 µg pCMV/fish.
Group 5 Fish co-injected with the DNA vaccine (pP-IPNV) at a dose of 1 µg/fish and the plasmid having the cDNA sequence of *C. gariepinus* PACAP (pCMV-PACAP) at a dose of 0.05 µg of pCMV-PACAP/fish.
Group 6: Fish co-injected with pP-IPNV vaccine (1 µg/fish) with a negative control plasmid at a dose of 0.05 µg pCMV/fish.

At 30 days post-vaccination, the fish were exposed to the virus by intraperitoneal injection of 100 µL of IPNV (1×10$^7$ $TCID_{50}$ mL$^{-1}$ per fish).

At day 7 post-infection, 10 fish were sacrificed per group and the viral load was assessed in head kidney.

Figure 7:
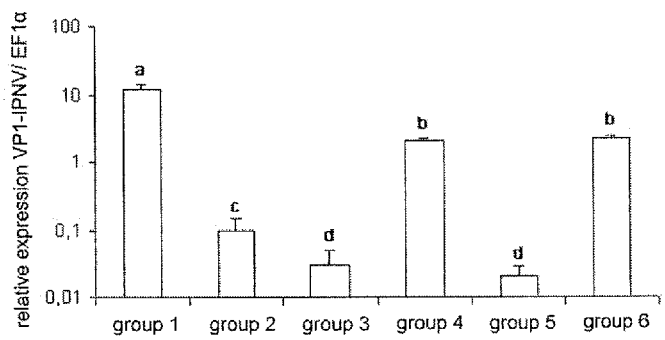
FIG. 7. Effect of the co-administration, by intramuscular injection, of the DNA vaccine (pP-IPNV) at a dose of 1 µg/fish with a plasmid DNA having the *Clarias gariepinus* PACAP cDNA, under the control of the immediate early promoter of the human cytomegalovirus (pCMV-PACAP). At day 30 post-vaccination, fish were exposed to the virus by intraperitoneal injection of 100 µL of IPNV ($1\times10^7$ (TCID$_{50}$) ml$^{-1}$ per fish). At day 7 post-infection, 10 fish per group were sacrificed in order to evaluate the viral load in head kidney by real time RT-PCR. Values represent the mean±standard deviation. Different letters in superscript represent statistically significant differences between groups. Group 1: injected with PBS, Group 2: injected with pP-IPNV at a dose of 1 µg/fish, Group 3: co-injected with pP-IPNV (1 µg/fish) and pCMV-PACAP (0.5 µg/fish), Group 4: co-injected with pP-IPNV (1 µg/fish) and pCMV (0.5 µg/fish), Group 5: co-injected with pP-IPNV (1 µg/fish) and pCMV-PACAP (0.05 µg/fish), Group 6: co-injected with pP-IPNV (1 µg/fish) and pCMV (0.05 µg/fish).

To determine the viral load, RNA was isolated from individual samples and it was performed the RT-PCR from 1 µg of RNA. Detection of VP1 gene expression was assessed by real time PCR. The results are shown in FIG. 7.

Co-administration of pP-IPNV and pCMV-PACAP decreased the viral load significantly, compared with the group that was co-injected with pP-IPNV and empty vectors. There were no differences between the doses of pCMV-PACAP tested.

Example 9

Effect of the Co-Administration of PACAP with a DNA Vaccine Based on the Gene Encoding the G Glycoprotein of VHSV, in Rainbow Trout (*O. mykiss*) Experimentally Challenged with Said Virus An experiment was conducted to evaluate the effect of the co-administration by intramuscular injection of *C. gariepinus* PACAP with a DNA vaccine based on the gene encoding the G glycoprotein of VHSV (pG-VHSV) in rainbow trout experimentally challenged with this virus. Four experimental groups were formed, each of 20 fish (10±2 g) and were kept in water at 10-12° C.:

Group 1: Fish injected with PBS.
Group 2: Fish injected with the DNA vaccine pG-VHSV (0.01 µg/fish).
Group 3: Fish co-injected with the DNA vaccine pG-VHSV at a dose of 0.01 µg/fish and *C. gariepinus* PACAP at a dose of 0.1 µg of PACAP/fish.
Group 4: Fish co-injected with the DNA vaccine pG-VHSV at a dose of 0.01 µg/fish and *C. gariepinus* PACAP at a dose of 0.5 µg of PACAP/fish.

Figure 8:
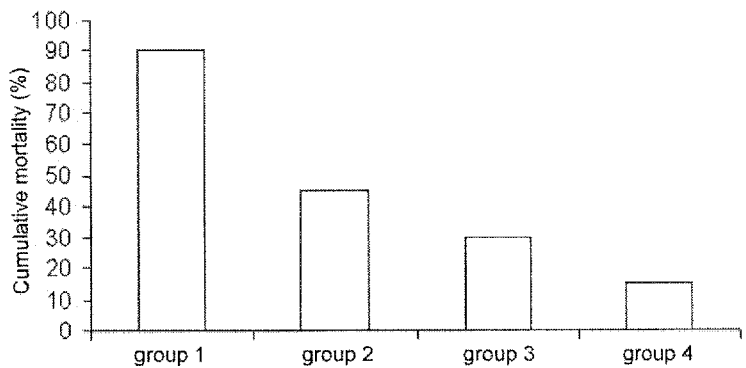
FIG. 8. Cumulative mortality of rainbow trout immunized intramuscularly with a DNA vaccine based on the gene encoding to the glycoprotein G of the VHSV (pG-VHSV) and the peptide PACAP. At week 4 post-vaccination fish were exposed to the virus ($1 \times 10^5$ TCID$_{50}$ mL$^{-1}$ per fish) by immersion baths. Cumulative mortality was assessed during 4 weeks post-challenge. Group 1: injected with PBS. Group 2: injected with pG-VHSV (0.01 µg/fish), Group 3: injected with pG-VHSV (0.01 µg/fish) and PACAP (0.1 µg/fish), Group 4: injected with pG-VHSV (0.01 µg/fish) and PACAP (0.5 µg/fish).

At 4 weeks post-vaccination the fish were exposed to the virus by immersion baths. The challenge was performed for 2 h in water containing a VHSV infective dose (1×10$^5$ $TCID_{50}$ per fish mL$^{-1}$). Cumulative mortality was assessed 4 weeks post-challenge and the results are shown in FIG. 8.

The co-administration of the peptide with the DNA vaccine reduced the mortality at 15% and 29% compared with the administration of the DNA vaccine alone, at the doses of 0.1 and 0.5 µg of PACAP/fish, respectively.

Example 10

Effect of the Administration of PACAP on Survival of Channel Catfish (*Ictalurus Punctatus*) after Immunization with Theronts of Ciliated Parasite *Ichthyophthirius Multifiliis*

An experiment was conducted to evaluate the effect of PACAP administration, after immunization with ciliated parasite theronts *I. multifiliis*, on survival of channel catfish (*I. punctatus*). The vaccination and challenge procedure was performed as proposed by Wang and Dickerson ((2002) Clinical and Diagnostic Laboratory Immunology 9 (1), 176-181). Four experimental groups of 25 fish (12±5 g) each one were established:

Group 1: Fish immunized on days 1 and 35 with PBS.
Group 2: Fish immunized on day 1 with 8000 live theronts *I. multifiliis* and at day 35 with 10,000 living theronts parasite.
Group 3: Fish immunized on day 1 with 8000 live theronts *I. multifiliis* and at day 35 with 10,000 living theronts parasite. These fish also received by immersion baths the neuropeptide PACAP at a dose of 100 µg of PACAP/L of water. The treatment was performed for 1 hour, on alternate days, in the two weeks prior to challenge (six immersion baths).

Group 4: Fish immunized on day 1 with 8000 live theronts *I. multifiliis* and at day 35 with 10,000 living theronts parasite. These fish were also subjected to immersion baths for 1 hour without PACA, by a procedure similar to Group 3.

Prior to the immunizations fish were treated with formalin to remove existing ectoparasites. The fish were maintained at 23±2° C. and continuous water flow. At day 84, the fish were challenged with 15 000 theronts. Mortality data were obtained within 30 days after challenge. The results are shown in Table 2. These results show a 27% increase in survival of the immunized fish which was simultaneously treated with PACAP.

TABLE 2

Survival of *I. punctatus* immunized and challenged with live theronts of *I. multifiliis*, after treatment with PACAP by immersion baths.

| Experimental groups | Challenged fish/ surviving fish | Survival (%) |
| --- | --- | --- |
| PBS | 25/0 | 0 |
| Live theronts | 25/15 | 60 |
| Live theronts + PACAP ib | 25/22 | 87 |
| Live theronts + ib | 25/14 | 56 | ib: These fish were subjected to 6 immersion baths for 1 hour, on alternate days in the two weeks prior to challenge

The invention claimed is:

1. A vaccine composition comprising a pituitary adenylate cyclase activating peptide (PACAP), at least one vaccine antigen specific for an infectious agent, and a pharmaceutically acceptable vehicle or diluent, wherein said PACAP and said vaccine antigen are present in an amount sufficient for producing protection to an infectious disease caused by the infectious agent in fish.

2. The composition of claim 1 which is formulated to be administered orally, by injection, or by immersion baths.

3. The composition of claim 2 wherein the PACAP (1) is in a concentration of 50 to 750 µg/Kg of feed if the composition is applied as a formulated feed, (2) produces a concentration of 0.1-10 µg per gram of body weight if it is applied by injection, or (3) produces a concentration of 50-1000 µg per liter of water if the composition is applied by immersion baths.

4. The composition of claim 1 wherein the PACAP is obtained by a) isolation from its natural source, b) by chemical synthesis, or c) by recombinant DNA technology.

5. The composition of claim 4 wherein the PACAP (1) is in a concentration of 50 to 750 µg/Kg of feed if the composition is applied as a formulated feed, (2) produces a concentration of 0.1-10 µg per gram of body weight if it is applied by injection, or (3) produces a concentration of 50-1000 µg per liter of water if the composition is applied by immersion baths.

6. The composition of claim 1 wherein the PACAP is obtained by administering a vector comprising cDNA coding for the PACAP.

7. A vaccine combination comprising a pituitary adenylate cyclase activating peptide (PACAP) and at least one vaccine antigen specific for an infectious agent, wherein said PACAP and said vaccine antigen are present in an amount sufficient for producing protection to an infectious disease caused by the infectious agent in fish and are administered in a same immunization schedule.

8. The combination of claim 7 wherein the PACAP and the antigen are formulated to be administered simultaneously, separately or sequentially during the same immunization schedule.

9. The combination of claim 8 wherein the PACAP (1) is in a concentration of 50 to 750 µg/Kg of feed if the combination is applied as a formulated feed, (2) produces a concentration of 0.1-10 µg per gram of body weight if it is applied by injection, or (3) produces a concentration of 50-1000 µg per liter of water if the combination is applied by immersion baths.

10. A method for increasing immune response to a vaccine antigen in a fish comprising administration of the composition of claim 1 to the fish.

11. The method of claim 10 wherein the composition is administered simultaneously, separately or sequentially during the same immunization schedule.

12. The method of claim 10 wherein the PACAP peptide is obtained by a) isolation from its natural source, b) by chemical synthesis, or c) by recombinant DNA technology; or as a nucleic acid.

* * * * *